(12) United States Patent
Manni et al.

(10) Patent No.: US 11,084,854 B2
(45) Date of Patent: Aug. 10, 2021

(54) PROTEASE-RESISTANT NEUROTROPHIC PEPTIDE FOR THE THERAPEUTIC TREATMENT OF NEURODEGENERATIVE AND/OR SKIN DISEASES

(71) Applicant: CONSIGLIO NAZIONALE DELLE RICERCHE, Rome (IT)

(72) Inventors: Luigi Manni, Monte Porzio Catone (IT); Marzia Soligo, Castelgandolfo (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 16/991,517

(22) Filed: Aug. 12, 2020

(65) Prior Publication Data
US 2021/0047379 A1 Feb. 18, 2021

(30) Foreign Application Priority Data
Aug. 12, 2019 (IT) .................. 102019000014646

(51) Int. Cl.
*C07K 14/475* (2006.01)
*A61P 25/28* (2006.01)
*C07K 16/22* (2006.01)

(52) U.S. Cl.
CPC ............ *C07K 14/475* (2013.01); *A61P 25/28* (2018.01); *C07K 16/22* (2013.01)

(58) Field of Classification Search
CPC ........ C07K 14/475; C07K 16/22; A61P 25/28
See application file for complete search history.

(56) References Cited

U.S. PATENT DOCUMENTS

2008/0050776 A1 2/2008 Neet et al.
2018/0086805 A1 3/2018 Cattaneo et al.

FOREIGN PATENT DOCUMENTS

WO 2013092776 A1 6/2013
WO WO-2013092776 A1 * 6/2013 ............. C07K 14/48

OTHER PUBLICATIONS

Paoletti et al. "Direct intracellular selection and biochemical characterization of a recombinant anti-proNGF single chain antibody fragment", Arch Biochem Biophys. Jun. 1, 2012;522(1):26-36 (Year: 2012).*

Bost et al. "Antibodies AGinast A Peptide Sequence Within the HIV Envelope Protein Crossreacts With Human Interleukin-2", Immunological Investigation, 1988, 17:577-586, see entire document (Year: 1988).*
Bendayan "Possibilities of False Immunocytochemical Results Generated by the Use of Monoclonal Antibodies: The Example of the Anti-proinsulin Antibody", J. Histochem. Cytochem. 1995; 43:881-886, see entire document (Year: 1995).*
The Merck Manuals Online Medical Library, [online]. Whitehouse Station, NJ: Merck Research Laboratories, 2006-2007. [retrieved on Dec. 8, 2020], Retrieved from the Internet: < URL: https://www.merckmanuals.com/professional/neurologic-disorders/prion-diseases/creutzfeldt-jakob-disease-cjd?query=cjd#>.*
Italian Search Report and Written Opinion for IT Patent Application No. 201900014646, dated Jun. 8, 2020, 11 pages.
Soligo, M et al: "homo sapiens pro-nerve growth factor long variant NGF(mRNA) complete eds, alternatively spliced", Aug. 22, 2018, XP2785283, Database accession No. MH358394, 1 page.
Pagadala P. C. et al: "Construction of a mutated pro-nerve growth factor resistant to degradation and suitable for biophysical and cellular utilization", Proceedings of the National Academy of Sciences, vol. 103, No. 47, Nov. 21, 2006 (Nov. 21, 2006), pp. 17939-17943, XP055290825, ISSN: 0027-8424, DOI: 10.1073/pnas.0604139103.
Soligo Marzia et al: "Different responses of PC12 cells to different pro-nerve growth factor protein variants", Neurochemistry International, Elsevier, Amsterdam, NL, vol. 129, Jul. 3, 2019 (Jul. 3, 2019), XP085765088, ISSN: 0197-0186, DOI: 10.1016/J.NEUINT.2019.104498. 13 pages.
Fahnestock Margaret et al: "ProNGF: a neurotrophic or an apoptotic molecule?", NGF and Related Molecules in Health and Disease : [7th International Conference on NGF and Related Molecules Held in Modena, Italy From May 15 to May 19, 2002]; In: Progress in Brain Research , ISSN 0079-6123 ; vol. 146, vol. 146, Jan. 1, 2004 (Jan. 1, 2004), -May 19, 2002 (May 19, 2002), pp. 101-110, XP055511295, NL, DOI: 10.1016/S0079-6123(03)46007-X, ISBN: 978-0-444-51472-1.
Ullrich A et al.: "Human Beta-Nerve Growth Factor Gene Sequence Highly Homologous to That of Mouse", Nature, MacMillan Journals Ltd, London, vol. 303, Jun. 30, 1983 (Jun. 30, 1983), pp. 821-825, XP002073892, ISSN: 0028-0836, DOI: 10.1038/303821A0.
Bruno M. A. et al: "Activity-dependent release of precursor nerve growth factor, conversion to mature nerve growth factor, and its degradation by a protease cascade", Proceedings of the National Academy of Sciences, vol. 103, No. 17, Apr. 25, 2006 (Apr. 25, 2006), pp. 6735-6740, XP055699893, ISSN: 0027-8424, DOI: 10.1073/pnas.0510645103.

* cited by examiner

*Primary Examiner* — Sharon X Wen
*Assistant Examiner* — Peter Johansen
(74) *Attorney, Agent, or Firm* — Armstrong Teasdale LLC

(57) ABSTRACT

A protease-resistant neurotrophic peptide is provided. A pharmaceutical composition including the protease-resistant neurotrophic peptide in a pharmaceutically acceptable carrier, in combination with optional adjuvants, stabilizers and/or preservatives, is also provided.

11 Claims, 8 Drawing Sheets
Specification includes a Sequence Listing.

A. w/o serum
B. serum
1. mature mNGF
2. proNGF-A wt
3. proNGF-A KG-RG
4. proNGF-A A73Y/KG-RG
5. purified proNGF-A

PROTEASE-RESISTANT NEUROTROPHIC PEPTIDE FOR THE THERAPEUTIC TREATMENT OF NEURODEGENERATIVE AND/OR SKIN DISEASES

The present invention falls within the field of therapeutic treatments of acute or chronic neurodegenerative diseases, trauma to the nervous system, and epithelial/cutaneous diseases.

Neurodegenerative diseases are diseases of extreme clinical and epidemiological relevance, with a considerable socio-economic impact, but at the same time characterized by the lack of effective therapeutic treatments.

Alzheimer's Disease, Parkinson's disease and Huntington's Chorea are among the most representative examples of chronic neurodegenerative forms that tend to arise and worsen with age. Since they are associated with a progressive structural and functional alteration of the central nervous system (CNS), these diseases involve a gradual and progressively disabling impairment of the patient's mental and cognitive faculties, as well as his/her motor functions.

Neurodegenerative processes also occur following a vascular or traumatic, acute brain damage. Among these, ischemic stroke is one of the world's main causes of disability and death, and the incidence of this disease also increases with age. In most cases, stroke is caused by thrombosis of the main cerebral arteries. The ischemic event shares several pathophysiological mechanisms with traumatic brain injury (TBI) that statistics indicate as the leading cause of death among individuals under the age of 44, and both of these pathological phenomena triggered by acute episodes lead to severe, both motor and cognitive, debilitating deficiencies.

In recent years, an increasing amount of experimental evidence has demonstrated that acute and chronic neurodegenerative diseases, although differing in symptoms, initial underlying causes and brain areas affected by the damage, exhibit common pathogenetic mechanisms which together contribute to cause the high degree of neuronal death primarily characterizing the onset and progression of these diseases. The Nerve Growth Factor (NGF) protein was the first neurotrophin to be identified in the 1950s and its biological effects on neuronal proliferation and survival and nerve fibre growth are well known. NGF, like other secreted proteins, is synthesized from a precursor protein, the pro-nerve growth factor (proNGF), which can be processed into mature neurotrophin inside the cell by proteolytic enzymes, such as for example furin, designated as pro-protein convertase or pro-convertase, or alternatively can be secreted and subject to proteolytic events by extracellular proteases. The proNGF molecule has its own biological activity and several studies have shown a dualism between the action of this precursor and that of the mature neurotrophin (Fahnestock, M., et al. ProNGF: a neurotrophic or an apoptotic molecule? *Prog Brain Res*, 2004. 146: p. 101-10). In fact, proNGF can exert a neurotoxic effect, related to the activation of the p75-sortilin receptor complex, and a pro-apoptotic effect, the latter being responsible for cell death under physiological conditions, for example during development, as well as in the context of neurodegenerative diseases. In contrast, NGF is also attributed a neurotrophic role, being responsible for the differentiation and maintenance of the phenotypic characteristics of cholinergic neurons in the central nervous system and catecholaminergic neurons in the peripheral nervous system. So far, two main variants of the proNGF precursor have been identified in humans: a so-called "long" variant composed of 296 amino acids, designated as proNGF-A, and a so-called "short" variant with a length of 221 amino acids, designated as proNGF-B. The proNGF-B variant was the first to be identified by cloning the corresponding encoding gene (Ullrich A et al.; Human beta-nerve growth factor gene sequence highly homologous to that of mouse *Nature*. (1983) 303(5920):821-5). Mature NGF factor originates from the carboxy-terminal portion of this protein by proteolytic cleavage. Subsequently, the work described in Soligo M. et al, 2019. Different responses of PC12 cells to different pro-nerve growth factor protein variants, Neurochem. Int., revealed the presence of the proNGF-A variant whose coding sequence is accessible from the NCBI database at the following link: https://www.ncbi.nlm.nih.gov/nuccore/MH358394.

Said coding sequence is herein designated as SEQ ID NO. 2.

In recent years, the use of the NGF peptide has been examined as a therapeutic opportunity for the treatment of neurodegenerative diseases, based on the neurotrophic and neurotropic potential of this peptide. Currently, clinical trials are underway to verify the potential therapeutic application of the NGF peptide in the ophthalmological field, whose therapeutic efficacy has already been approved for the treatment of neurotrophic keratitis. Recently, the NGF peptide was also used in the treatment of a severe clinical case of brain trauma, by intranasal administration (Chiaretti, A., et al., 2017. Intranasal Nerve Growth Factor administration improves cerebral functions in a child with severe traumatic brain injury: A case report. Brain Inj 31, 1538-1547). However, the therapeutic use of this neurotrophin suffers from some major limitations, which derive from the hyperalgesic effect of the NGF peptide as well as from its susceptibility to degradation by extracellular matrix proteases.

Patent application IT102018000003279 describes the use of the proNGF-A variant for the therapeutic treatment of acute or chronic neurodegenerative diseases and inflammatory diseases, which is made possible by the significant neuroprotective activity exhibited by said variant as well as by its superior pharmacological safety profiles compared to NGF.

Although, on the basis of what is described in Soligo M. et al, 2019. Different responses of PC12 cells to different pro-nerve growth factor protein variants, Neurochem. Int., the proNGF-A variant exhibits high resistance to the action of extracellular matrix proteases compared to the NGF and proNGF-B peptides, a feature that allows it to be produced and isolated with high purity, its large-scale production by both prokaryotic and eukaryotic heterologous expression systems is however particularly difficult due to the sensitivity of the proNGF-A peptide to the action of endocellular proteases called pro-convertases. Studies carried out by the present inventors have in fact revealed that, in the producer cell, the proNGF-A peptide undergoes a proteolytic digestion which causes the loss of an N-terminal fragment of about 60 amino acids in length, causing it to dangerously turn into the neurotoxic proNGF-B variant (FIG. 1, left panel). In addition, in the producer cell, both proNGF-A and proNGF-B are further metabolised by the furin protease, resulting in their at least partial conversion into the NGF peptide (Bruno, M. A. et al., 2006. Activity-dependent release of precursor nerve growth factor, conversion to mature nerve growth factor, and its degradation by a protease cascade. Proc Natl Acad Sci USA 103, 6735-6740), the only protein variant released and detectable in the culture medium (FIG. 1, right panel).

In this context, therefore, the dramatic need arises for the development of suitable strategies to allow efficient production of the proNGF-A peptide, more particularly a large-scale production, preferably on an industrial scale, thus allowing the use of said peptide in the clinical-therapeutic field, and the beneficial effects from the administration thereof.

This need has been met by the present inventors, who first isolated a new mutant of the human proNGF-A peptide and surprisingly found that said mutant peptide is particularly resistant to attack by the endocellular pro-convertase enzymes, thereby preventing its proteolytic processing into the neurotoxic proNGF-B variant within the producer cell, while maintaining the biological properties and functions, in particular the marked neurotrophic and neuroprotective activity, of the native peptide unchanged.

Therefore, one object of the present invention is an isolated peptide, hereinafter designated as human proNGF A isoform A73Y/KG-RG (hproNGF-A A73Y/KG-RG), which consists of the amino acid sequence SEQ ID NO. 3.

The hproNGF-A A73Y/KG-RG peptide according to the invention is characterised in that it has a molecular weight of 32-34 kDa, high resistance to degradation by the extracellular proteases plasmin and matrix metalloproteases (MMP), as well as to degradation by enzymes of the intracellular pro-convertase family called "proprotein convertases subtilisin/kexin-like(PCSK)1-9", which include, for example, the enzymes furin, PC1/3, PC2, PC4 and PACE4. The peptide according to the invention has a length of 296 amino acids and a theoretical isoelectric point of about 9.5.

Compared to the previously known human native hproNGF-A variant, the amino acid sequence of which is herein designated as SEQ ID NO. 1, the peptide according to the invention contains three amino acid substitutions in its primary structure (FIG. 2). More specifically, the amino acid sequence of the mutated peptide according to the invention, herein designated as SEQ ID NO. 3, comprises the substitution of an alanine residue with a tyrosine residue at position 73 (A73Y), the substitution of a lysine residue with a glycine residue at position 175 (K175G), and the substitution of an arginine residue with a glycine residue at position 176 (R176G).

As will be described in detail in the following experimental section, the present inventors succeeded in isolating the mutated hproNGF-A peptide of the invention by means of a sequential site-directed mutagenesis approach based on the PCR method, using the nucleotide sequence encoding the native hproNGF-A peptide as the template for the amplification reaction. This approach generated a series of coding sequences carrying different mutations at different positions, whose expression in suitable cell systems led to the production of the corresponding mutated hproNGF-A peptides. Surprisingly, the analysis of these mutants revealed only one proNGF-A peptide structurally stable to the action of intracellular proteases. Subsequent analysis of the nucleotide sequence encoding said mutated proNGF-A peptide showed, for the first time, the presence of a unique combination of three point mutations located in the regions supposedly responsible for the transformation of the proNGF-A peptide into the proNGF-B peptide, and the further transformation into the NGF peptide.

Compared to the native nucleotide sequence SEQ ID NO. 2, the nucleic acid sequence identified for the first time by the present inventors is characterised in that it comprises the following nitrogenous base mutations: substitution of a guanine with a thymine (G>T transversion) at position 217, substitution of a cytosine with an adenine (C>A transversion) at position 218, and substitution of a guanine with a thymine (G>T transversion) at position 219, said mutations corresponding to the amino acid substitutions A73Y, K175G and R176G, respectively, in the mutated hproNGF-A peptide, as defined above (FIG. 2).

Therefore, a further object of the invention is an isolated nucleic acid sequence (cDNA) comprising or consisting of SEQ ID NO. 4, as well as a peptide which is encoded by nucleic acid sequence SEQ ID NO: 4.

An isolated monoclonal or polyclonal antibody that specifically binds the mutated peptide of the invention also falls within the scope of the present invention. Techniques for obtaining polyclonal and monoclonal antibodies are well established and the person skilled in the art is able to apply them, without having to resort to any inventive step, in order to obtain the antibody of the invention.

A further object of the present invention is an expression vector comprising the nucleic acid sequence as defined above, i.e. SEQ ID NO. 4, and optionally further comprising a promoter sequence and a polyadenylation signal sequence, as well as a host cell comprising the above expression vector.

Recombinant expression vectors for use in the manufacture of peptides or proteins are known and described in the state of the art, therefore the selection and use thereof are within the skills of those of ordinary skill in the art. Such vectors can be prokaryotic or eukaryotic vectors. By way of non-limiting example, eukaryotic vectors for expression in insect cells such as pBacPAK8, pBacPAK9, pAcG2T, pAcHLT A, pAcHLT B, pAcHLT C, pAcGHLT A, pAcGHLT B, pAcGHLT C, pAcSG2, pBAC-1, pFastBac1, pFastBacHT, pFastBac-Dual, pAcP(+)IE1, pAcP(−)IE1, pAcUW31, pBAC-1, pBAC-2cp, pBAC-3, pBAC4x-1, pBAC-7, pBAC-8, pBAC-9, pBAC-10, pBacPAK8, pBacPAK9, pBACsurf-1, pBlueBac4.5, pBlueBacHis2, pMbac, pMelBac, pPbac, pTriEx-1, pVL1392, pVL1393, are mentioned. Alternatively, the vector according to the invention may be suitable for expression in mammalian cells, for example pcDNA3, pcDNA3.1(−), pcDNA3.1(−) myc-His A, pcDNA3.1(−) myc-His B, pcDNA3.1(−) myc-His C, pcDNA3.1(+), pcDNA3.1(+) myc-His A, pcDNA3.1 (+) myc-His B, pcDNA3.1(+) myc-His C, pcDNA3.1/Hygro (−), pcDNA3.1/Hygro(+), pcDNA3.1/V5-His A, pcDNA3.1/Zeo (−), pcDNA3.1/Zeo (+), pcDNA3.1+C-6His, pcDNA3.1+C-DYK, pcDNA3.1+C-DYK-P2A, pcDNA3.1+C-HA, pcDNA3.1+C-Myc, pcDNA3.1+N-6His, pcDNA3.1+N-DYK-P2A, pcDNA3.1+N-GST, pcDNA3.1+N-HA, pcDNA3.1+N-Myc, pcDNA3.1-C-eGFP, pcDNA3.1-N-eGFP, pcDNA3.1-P2A, pcDNA3.1-P2A-eGFP, pcDNA5/FRT, pcDNA5-TOpcDNA6/V5-His A, pCI-Neo, pCMV-3Tag-1°, pCMV-3Tag-1a-P2A, pCMV-3Tag-2°, pCMV-3Tag-3°, pCMV-3Tag-3a-P2ApCMV-3Tag-4°, pEGFP-N1, pGen2.1, pGL3-Basic, pGL4.10 [luc2], pGL4.14[luc2/Hygro], pGL4.17, pHLSec, pBABE, pBABE-puro). Alternatively, the vector for use according to the invention may be suitable for expression in yeast cells, for example pETCON, pYES2, pAO815, pGAPZ, pGAPZa, pHIL-D2, pHIL-S1, pPIC3.5K, pPIC9K, pPICZ, pPICZa, or for expression in bacterial cells, for example pBluescript II KS(−), pBluescript II KS(+), pBluescript II SK(−), pBluescript II SK(+), pBluescript SK(+), pCDFDuet-1, pCOLA-Duet-1, pColdII, pET-11°, pET-11b, pET-11c, pET-11d, pET-14b, pET-15b, pET-16b, pET-17b, pET-19bpET-20b (+), pET-21a(+), pET-21b(+), pET-21d(+), pET-22b(+)pET-23a(+), pET-24a(+), pET-24b(+), pET-24c, pET-24c(+), pET-24d, pET-24d(+), pET-25b(+), pET-26b(+), pET-27b (+), pET-28a(+), pET-28b(+), pET-28c(+), pET-29a(+), pET-29b(+), pET-29c(+), PET-30a(+), PET-30b(+), PET-30c(+), PET-31b(+), pET-32a(+), pET-32b(+), pET-3°, pET-3b, pET-3c, pET-3d, pET-41a(+), pET-41b(+), pET-41c(+), pET-42a(+), pET-42b(+), pET-42c(+), pET-43.1a(+), pET-43.1b(+), pET-45b(+), pET-50b(+), pET-51b(+), pET-52b(+), pET-9°, pETDuet-1, pGEX-2TK, pGEX-4T-1, pGEX-4T-1-H(RBS), pGEX-4T-1-M(RBS), pGEX-4T-2 pGEX-4T-3, pGEX-5X-1, pGEX-5X-1-H(RBS), pGEX-5X-1-M(RBS), pGEX-5X-2, pGEX-5X-3, pGEX-6P-1, pGEX-6P-1-H(RBS), pGEX-6P-1-M(RBS), pGEX-6P-2, pGEX-6P-3, pGS-21°, pMAL-c4x, pMAL-c4x-1-H(RBS), pMAL-c4x-1-M(RBS), pMAL-c5E, pMAL-c5x, pMAL-p5E, pMAl-p5g, pMAl-p5x, pQE-1, PQE30, pQE32, pQE-60, pRSFDuet-1, pUC18, pUC19.

Restriction reactions, both with blunt-end technologies, for example Topo-cloning, and through methods such as TA cloning, GATEWAY Cloning Technology, In-Fusion, Ligation Independent Cloning (LIC), Di-o multi-cistronic cloning, GenEZ™ cloning, can be used to clone the nucleotide sequence encoding the mutated peptide according to the invention in a suitable vector as described above. In addition, tag sequences can be employed at the N- and/or C-terminus, as well as specific promoter sequences and specific polyadenylation signal sequences.

Preferably, the cell system used for the expression of the expression vector of the invention is selected from eukaryotic systems, for example insect cells such as SF-9, SF-21, High Five, Mimic, *Drosophila* S2, yeast cells, for example *S. cerevisiae* and *Pichia pastoris*, mammalian cells, for example CHO, BHK, HeLa, Hek293 cells, protozoan parasite cells such as *Leishmania tarentolae*. Alternatively, the cellular expression system may be a prokaryotic system, for example *E. coli* bacterial cells.

The present invention also relates to a method for the preparation of the mutated peptide of the invention, according to which the transformed host cell is cultured under suitable conditions and for a time sufficient for the expression of the peptide of the invention. Typically, suitable culture conditions and times depend on the cell system used and may be related, for example, to the composition of the culture medium, the pH, the relative humidity, the gaseous component of $O_2$ and $CO_2$, as well as the temperature. The selection of the most suitable culture conditions and times to be used in the method of the invention is well within the skills of those of ordinary skill in the art.

In a preferred embodiment, the method according to the invention additionally comprises the step of recovering the peptide produced from the cell culture. The recovery step can be carried out by using protein purification methods belonging to the prior art, for example protein denaturation, solubilization and/or renaturation, or one or more chromatographic and/or desalting steps, or still by ultrafiltration, dialysis and/or freeze-drying. As will be explained in more detail in the following experimental section, the present inventors, through studies carried out in vitro, have shown that the mutated peptide according to the invention has the ability to resist the action of intracellular proteases and maintain its primary structure intact during the metabolic events that lead to its synthesis, while preserving the lower sensitivity of the extracellular matrix to proteases, typical of the native variant.

The peptide of the invention is therefore particularly suitable to be produced according to methods used in pharmaceutical workshops and to be used in the therapeutic treatment of a neurodegenerative and/or neuro-traumatic and/or epithelial/cutaneous disease.

In the context of pathological events triggered by an acute, traumatic or vascular brain insult, mention can be made, for example, without limitation, of: (ischemic and hemorrhagic) stroke, traumatic brain injury, intracranial hypertension, cerebral edema, (perinatal, pediatric or adult) hypoxia/ischemia, hypoxia/ischemia caused by cardiac arrest, drowning or hypothermia.

With reference to chronic neurodegenerative disease patterns, mention can be made, for example, without limitation, of: Alzheimer's disease, Parkinson's disease, Huntington's Chorea, amyotrophic lateral sclerosis (ALS), progressive supranuclear palsy, frontotemporal dementia, Lewy body dementia, Creutzfeldt-Jakob disease (CJD), Gerstmann-Sträussler-Scheinker disease (GSS).

Diseases of the epithelia and skin include, but are not limited to, diabetic pressure ulcers, peripheral neuropathic ulcers, pressure sores in patients with myelomeningocele (spina bifida), skin ulcers due to infectious diseases (leprosy, AIDS), traumatic or neurothrophic corneal ulcers (neurotrophic keratitis), inflammatory chronic skin ulcers and vasculitis ulcers.

In a preferred embodiment, the peptide for use according to the invention is particularly suitable for the therapeutic treatment of a disease selected from the group consisting of (ischemic and hemorrhagic) stroke, traumatic brain injury, intracranial hypertension, cerebral edema, (perinatal, pediatric or adult) hypoxia/ischemia, hypoxia/ischemia caused by cardiac arrest, drowning or hypothermia, Huntington's Chorea, amyotrophic lateral sclerosis (ALS), progressive supranuclear palsy, frontotemporal dementia, Creutzfeldt-Jakob disease (CJD), Gerstmann-Sträussler-Scheinker disease (GSS), vasculitis, chronic inflammatory skin disease.

A pharmaceutical composition comprising the peptide as defined in appended claim 1 or 2, in combination with pharmaceutically acceptable carriers, excipients and/or diluents, is also within the scope of the invention.

The pharmaceutical composition for use according to the invention can be formulated into any suitable form, for example for enteral (oral or gastro-enteral, rectal, sublingual), parenteral (percutaneous, inhalation, ocular, intravenous, intra-arterial, intramuscular, intradermal, intranasal, subcutaneous, intraperitoneal) and topical administration (direct contact of the drug with the site of action and/or the skin and/or the mucous membranes and/or the ocular surface). Of course, the selection of suitable carriers, excipients and/or diluents is carried out depending on the desired form of administration and this selection is within the skills of those of ordinary skill in the art.

The experimental section that follows is provided for illustration purposes only and does not limit the scope of the invention as defined in the appended claims. In the experimental section, reference is made to the accompanying drawings, wherein:

FIG. 1 shows the cell lysates (left panel) and conditioned media (right panel) of producer cells, in which the empty vector (line 2), the vector containing the nucleotide sequence encoding native proNgf-A ("proNgf-A wt", line 3) or the vector containing the nucleotide sequence encoding native proNgf-B ("proNgf-B wt", line 4) have been expressed, respectively, compared with lysates from non-transfected cells (line 1).

FIG. 2 shows a schematic drawing of the structure of the pre-proNGF-A protein highlighting the portion in common with the proNGF-B peptide. In addition, the figure shows the positions where the amino acid mutations A73Y, K175G and R176G located in regions at the interface between proNGF-A and proNGF-B and between proNGF-A and mature NGF occur, and the corresponding nucleotide mutations, as summarized in the table at the bottom of the same figure.

Figure 5:
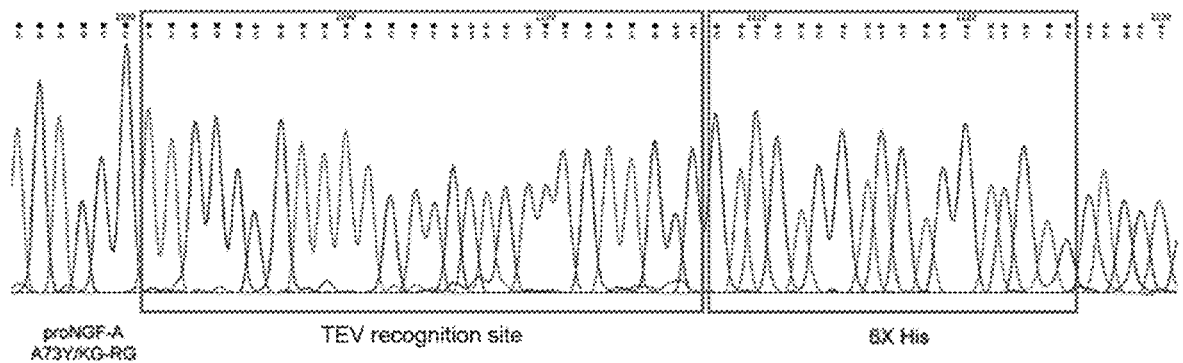

FIG. 5—upper panel—shows the mutated nucleotide sequence of proNgf-A A73Y/KG-RG in the step of the method comprising its insertion into the bacmid (SEQ ID NO. 11). On the other hand, the lower panel shows the result of the Sanger sequencing required to ascertain the correct insertion and orientation of proNgf-A A73Y/KG-RG in the bacmid relative to the recognition and cleavage sequence for the TEV enzyme and to the 6×His sequence, which is necessary during the purification step.

Figure 6A:
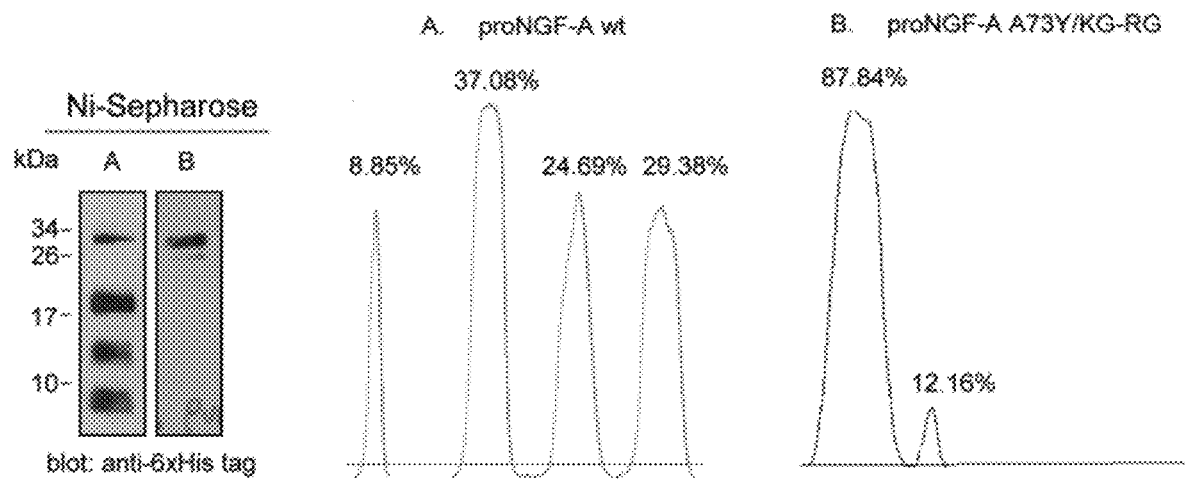
Figure 6B:
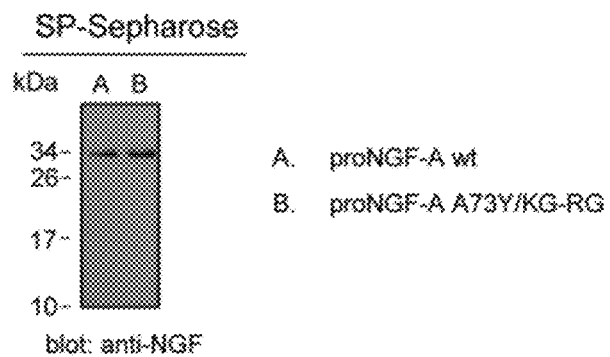

FIG. 6A, on the left, shows the products obtained after Ni-Sephasore chromatography of the native proNGF-A ("proNGF-A wt") (A) and proNGF-A A73Y/KG-RG (B) peptides. Panel A, on the right, also shows the results of densitometric analyses relating to the two products obtained. FIG. 6B shows the final product obtained after the second SP-Sepharose chromatography (A=native proNGF-A; B=proNGF-A A73Y/KG-RG).

Figure 7:
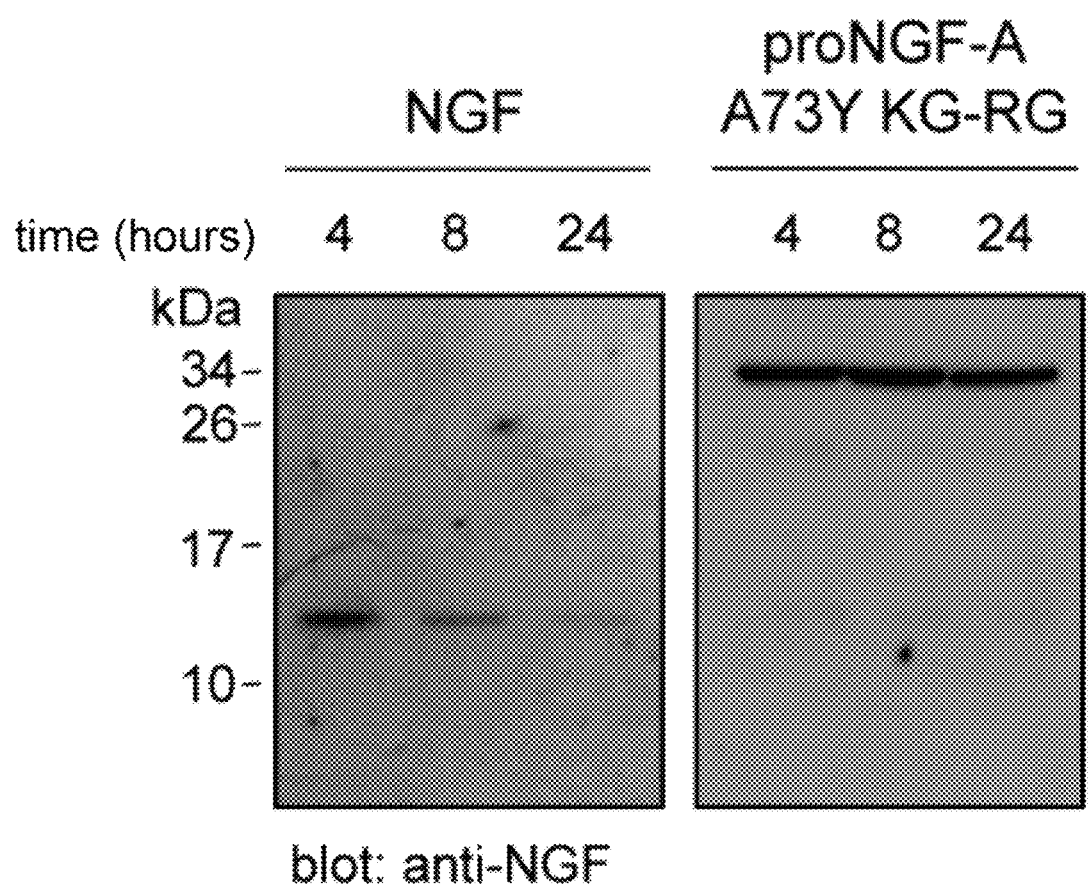

FIG. 7 shows the kinetics of the time of residence, in the culture medium, of NGF peptide (left panel) and proNGF-A A73Y/KG-RG peptide (right panel) used to treat PC12 cells.

Figure 8A:
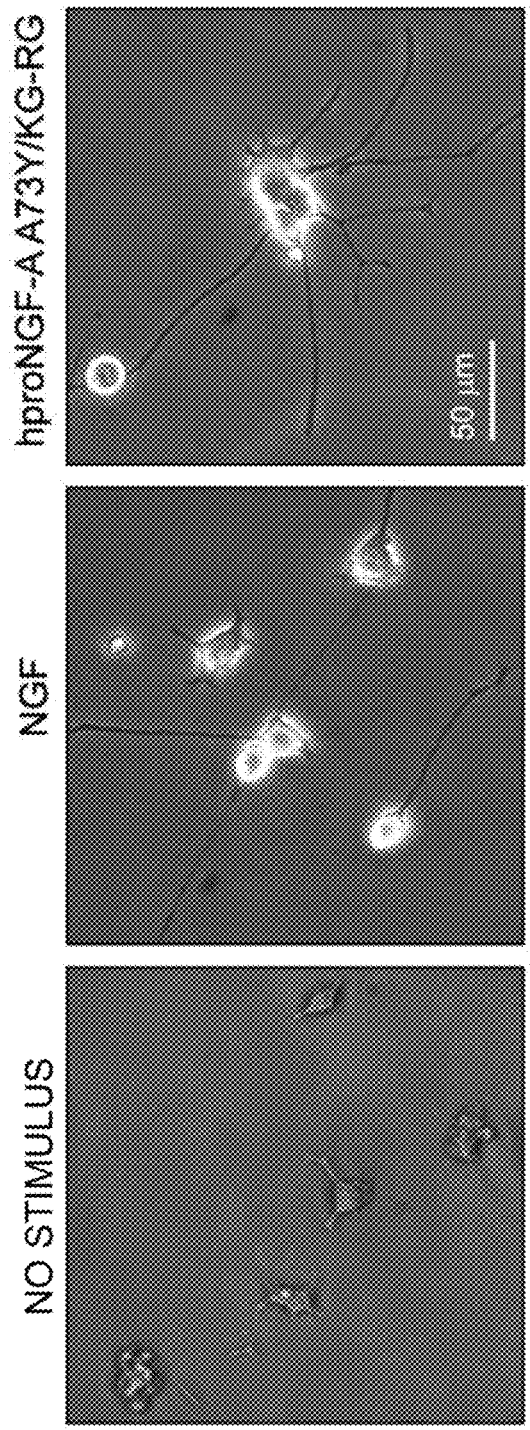
Figure 8B:
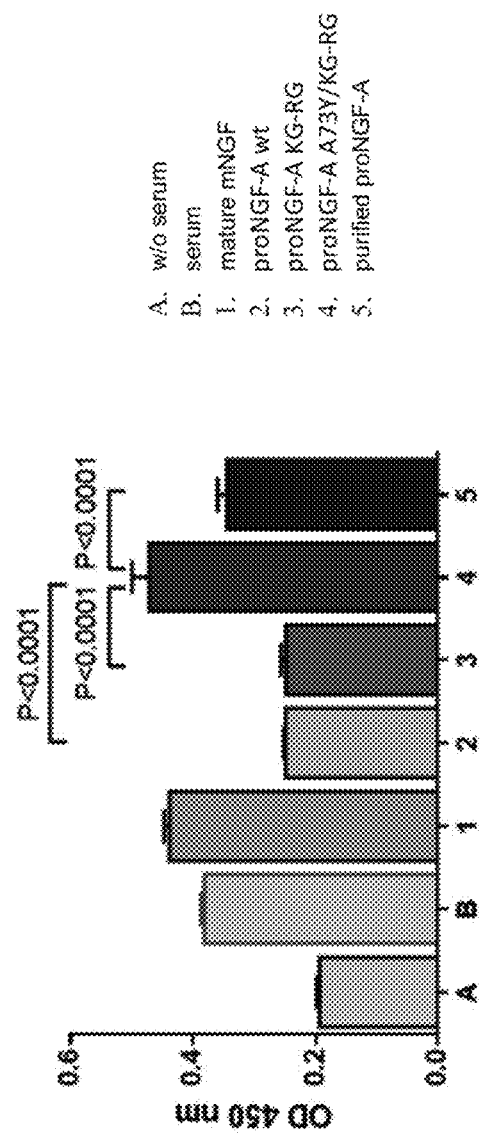

FIG. 8A shows a series of photomicrographs indicative of PC12 cell differentiation after exposure to serum-free medium (first picture from the left), NGF (second picture from the left), or proNGF-A A73Y/KG-RG (third picture from the left). The histogram in FIG. 8B shows absorbance values from the survival of PC12 cells maintained in medium w/o serum (bar A) and w/ serum (bar B), and treated, in the absence of serum, with mature NGF peptide (mNGF, bar 1), non-mutated proNGF-A peptide (proNGF-A wt, bar 2), proNGF-A KG-RG peptide (bar 3), proNGF-A A73Y/KG-RG peptide (bar 4), or treated with proNGF-A peptide purified from murine submandibular glands (bar 5). Native mNGF peptide vs proNGF-A wt (P<0.0001), native mNGF vs proNGF-A KG-RG (P<0.0001), native mNGF vs purified proNGF-A (P=0.0002), purified proNGF-A vs proNGF-A KG-RG (P=0.0002).

EXAMPLE 1: PRODUCTION OF HPRONGF-A A73Y/KG-RG BY A HETEROLOGOUS SYSTEM

The present inventors carried out a sequential site-directed mutagenesis approach in order to generate mutations in hproNGF-A-coding nucleotide sequence (SEQ ID NO. 2) which were capable of modifying the interaction of this protein with endocellular proteolytic enzymes (pro-convertases) responsible for converting hproNGF-A into the neurotoxic hproNGF-B variant in the producer cell. Coding nucleotide sequences containing different combinations of the single point mutations were obtained.

Said mutated sequences were cloned into a suitable expression vector, and the recombinant vectors thus obtained were then tested by transfection in host cells (for example HeLa or Hek 293 cells, as described in the following Example 2), for their ability to produce an intact protein which can be released as such into the culture medium.

Figure 1:
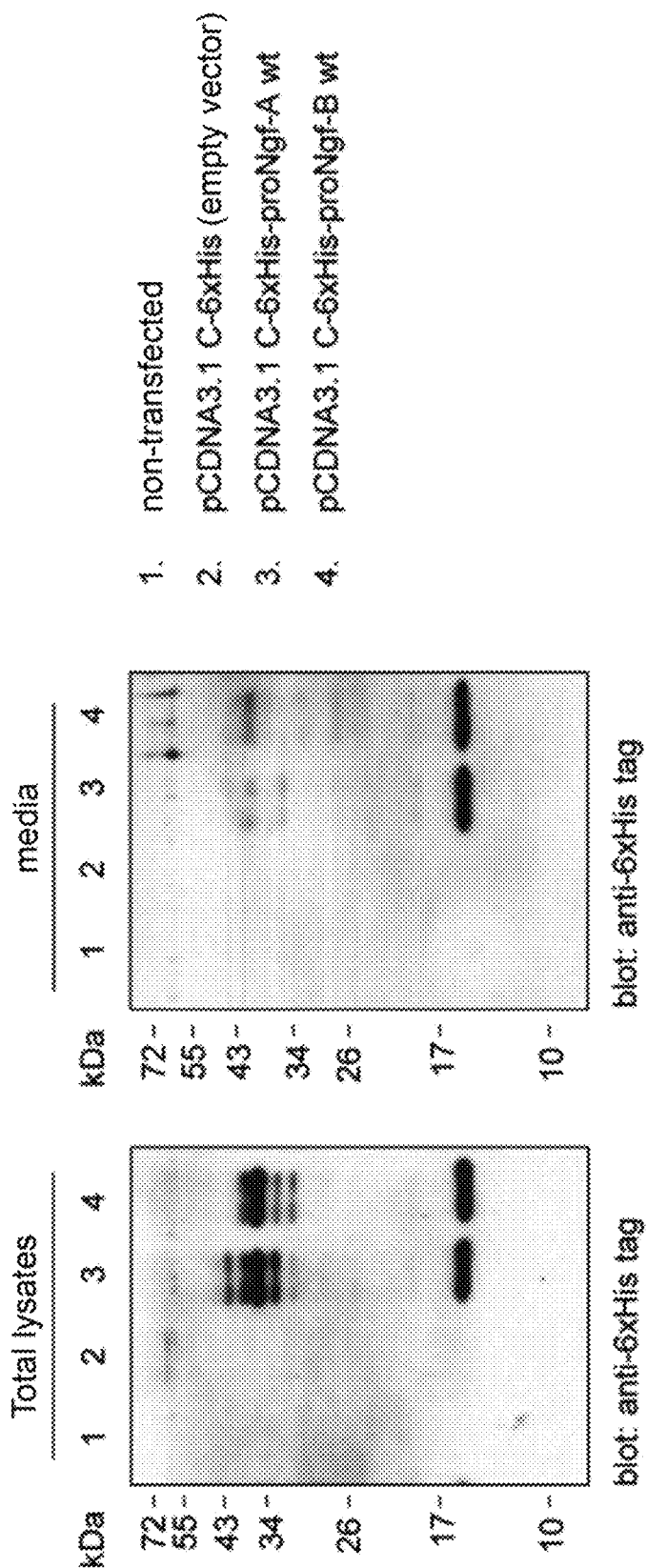
Figure 2:
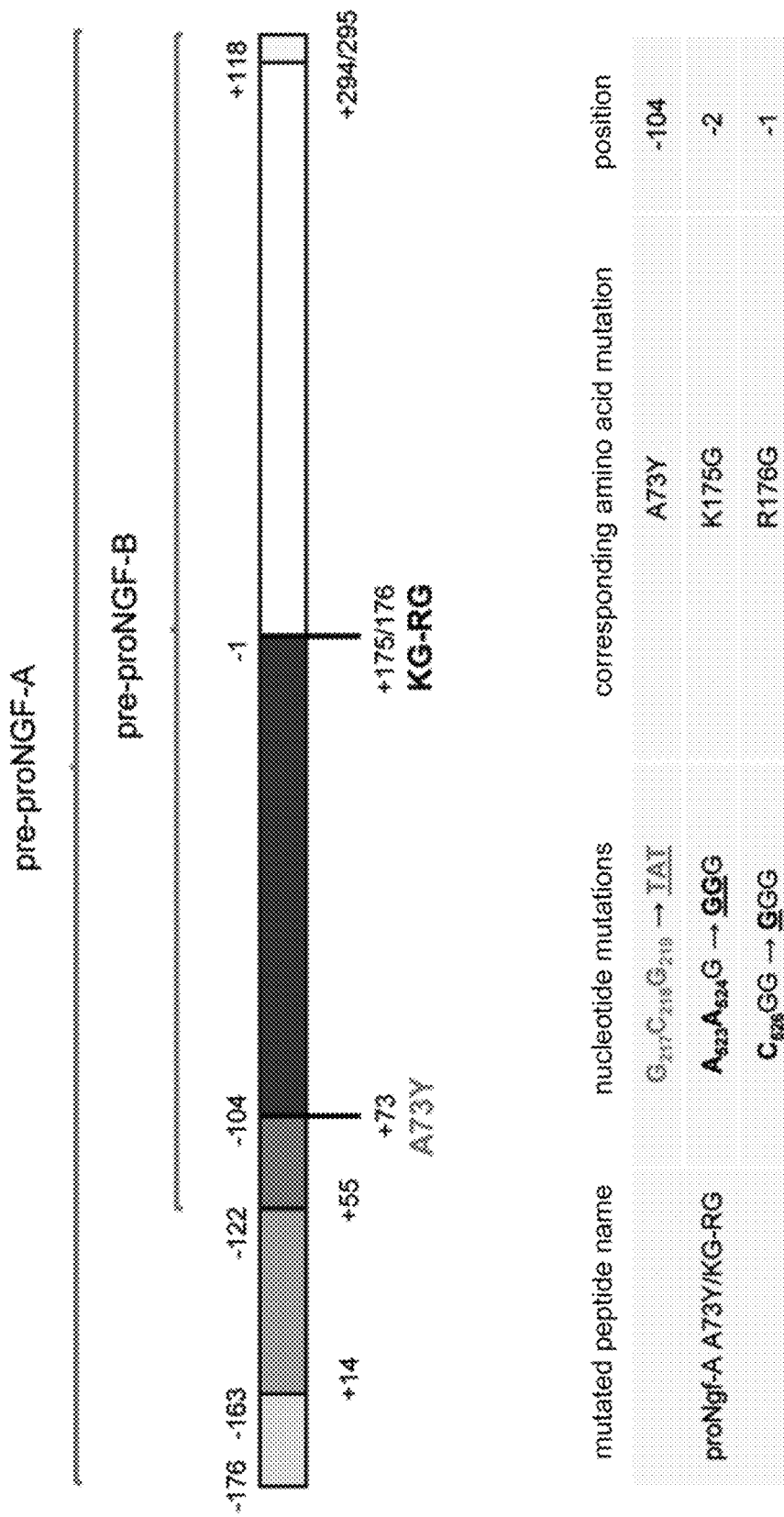
Figures 3A, 3B:
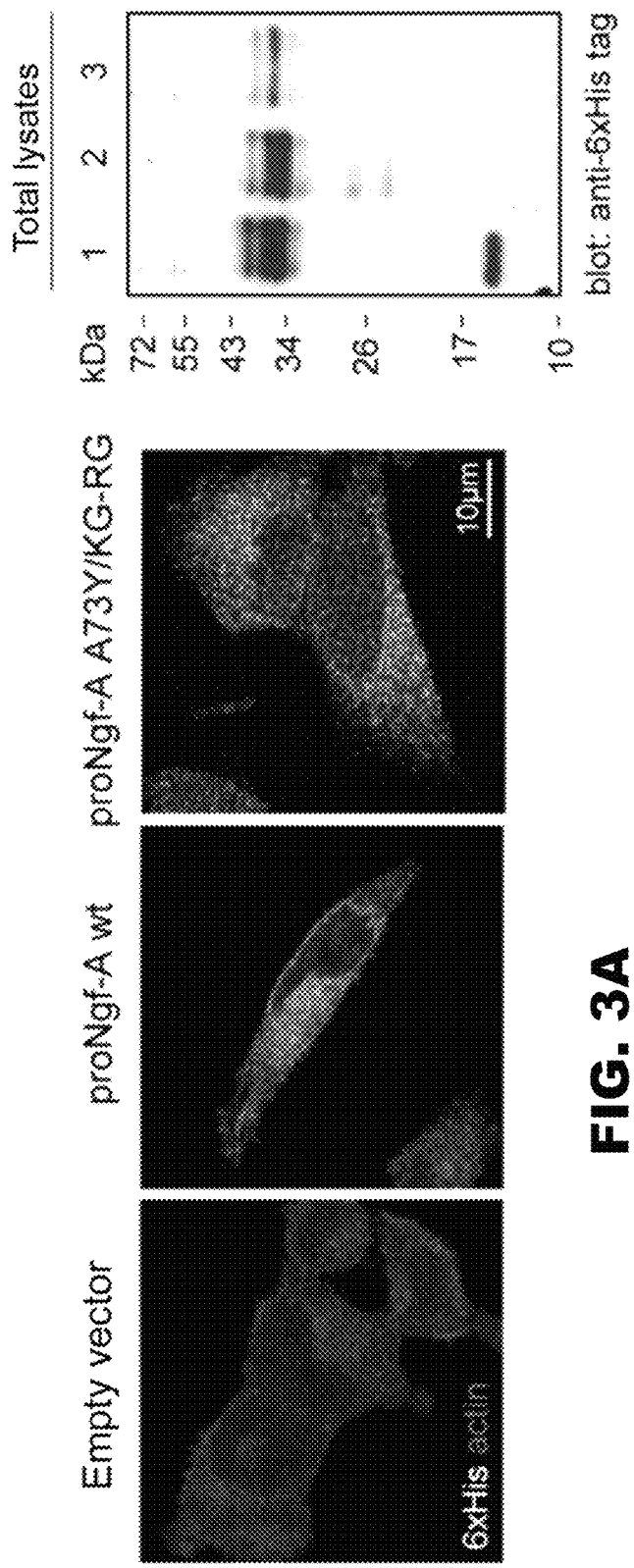
FIG. 3A shows photomicrographs of producer cells transfected with the empty vector (first image from the left), the vector containing the nucleotide sequence encoding native proNgf-A (second image from the left), and the vector containing the nucleotide sequence encoding proNgf-A A73Y/KG-RG (third image from the left), respectively.
FIG. 3B shows cell lysates of producer cells transfected with the plasmid expressing native proNgf-A, the plasmid expressing proNgf-A containing the KG-RG mutations alone, and the plasmid expressing proNgf-A containing the A73Y/KG-RG mutations.

The analysis carried out by the present inventors surprisingly revealed that only the recombinant construct expressing a peptide containing the mutation inserted in position 73 of native hproNGF-A sequence (SEQ ID NO. 1)—through conversion of the amino acid alanine to tyrosine (A73Y)—, in association with the double mutation K175G/R176G—in which lysine 175 is substituted with glycine, and arginine 176 is substituted with glycine—preserved the ability to be expressed and synthesized within the cell, as in the case of native, non-mutated hproNGF-A ("hproNGF-A wt") (FIG. 3, panel A).

This construct was also found to be capable of making the host cells produce a peptide corresponding to hproNGF-A in terms of molecular weight (Western blot, FIG. 3, panel B).

EXAMPLE 2: MUTATION OF THE SEQUENCE ENCODING THE HPRONGF-A PEPTIDE

In order to introduce one or more mutations into the hproNGF-A peptide coding sequence, a PCR reaction was set up by following the instructions for use of the QuikChange II site-directed Mutagenesis kit produced by Agilent Technologies (#200523). Pairs of forward and reverse primers, complementary to the region where the mutation is to be introduced, were used for amplifying the entire expression vector containing the hproNGF-A coding sequence. For the insertion of three mutations, therefore, two sequential PCRs were performed, each time using primer pairs having the following sequences:

```
A73Y Forward Primer:
                                      (SEQ ID NO. 5)
5'-GCTTTTCTGATCGGCATACAGTATGAACCACACTCAGAGAGCAAT-
3'

A73Y Reverse Primer:
                                      (SEQ ID NO. 6)
5'-ATTGCTCTCTGAGTGTGGTTCATACTGTATGCCGATCAGAAAAGC-
3'

K175G/R176G Forward Primer:
                                      (SEQ ID NO. 7)
5'-CAGGACTCACAGGAGCGGGGGGTCATCATCCCATCC -3'

K175G/R176G Reverse Primer:
                                      (SEQ ID NO. 8)
5'-GGATGGGATGATGACCCCCCGCTCCTGTGAGTCCTG-3'.
```

Figure 4:
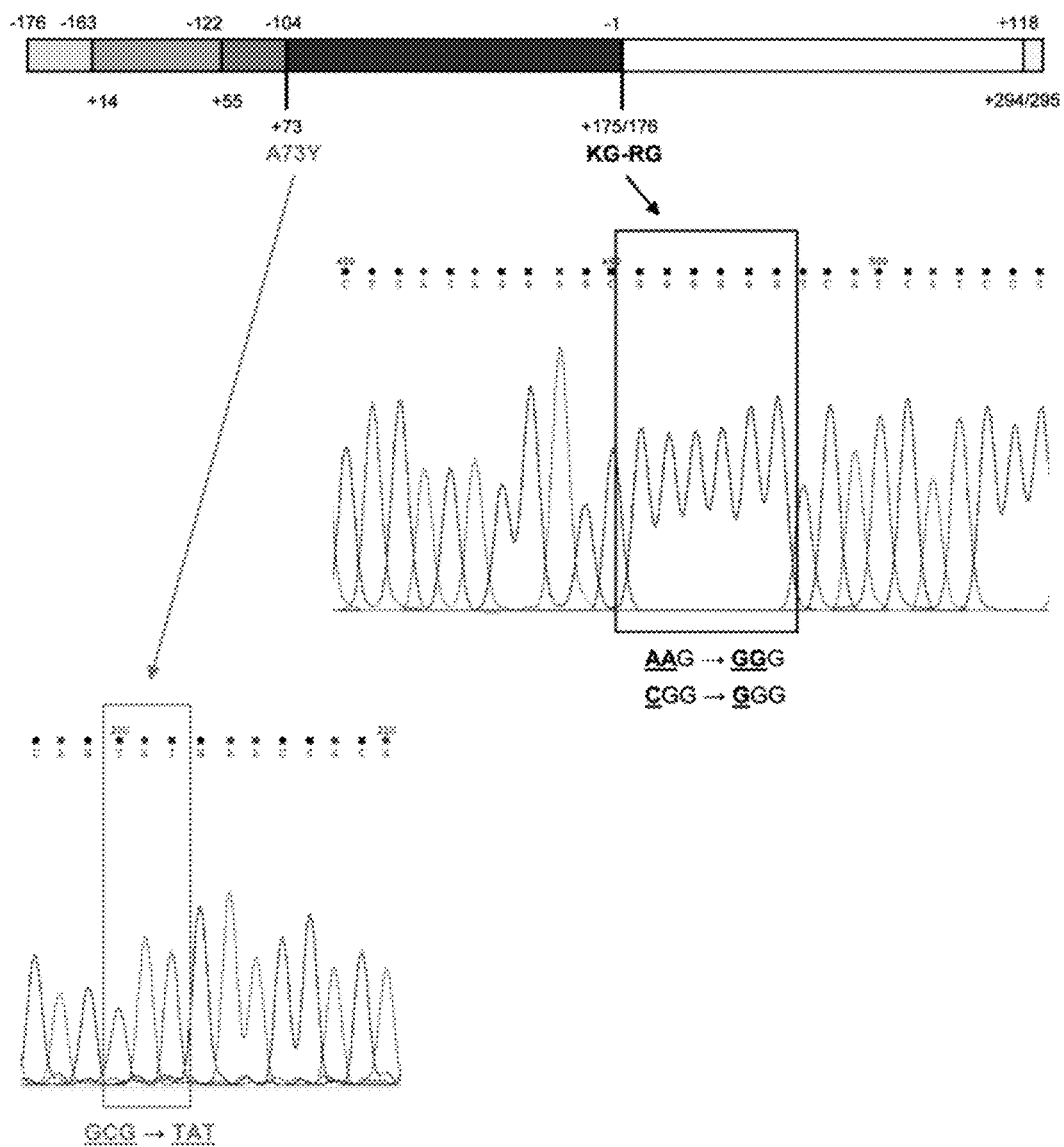
FIG. 4 shows the results of the Sanger sequencing that led to the identification of mutations corresponding to A73Y (bottom left) and KG-RG (right) in the nucleotide sequence encoding the proNGF-A peptide, with the nucleotide substitutions highlighted.

After carrying out the sequential mutagenesis processes, the resulting expression vectors containing the mutated hproNGF-A were used to transform XL1-Blue bacterial cells, which are highly competent for receiving and amplifying the plasmid DNA of interest, through the "heat-shock" method. The transformed bacteria were then seeded on Petri dishes containing solid agarose culture medium added with the antibiotic ampicillin, required for the selection of recombinant bacteria, which through the plasmid have also incorporated the gene for resistance to this antibiotic. An overnight incubation at 37° C. was sufficient to allow the growth of bacterial colonies resistant to the ampicillin contained in the solid culture medium. Colonies were then picked and used for plasmid DNA isolation by using the PureLink® HiPure Mini Plasmid Purification Kit (Catalog Number: K210002 Thermo Scientific), and following the instructions provided with the kit. These products could then be purified and checked for the inserted mutations by Sanger sequencing analysis, as shown in FIG. 4, performed at a highly specialized service company (Sequencing Core Facilities of Eurofins Genomics—Ebersberg, Germany).

EXAMPLE 3: CONSTRUCTION OF A BACULOVIRUS EXPRESSION SYSTEM FOR THE MANUFACTURE OF THE HPRONGF-A A73Y/KG-RG PEPTIDE

The plasmid containing the mutated DNA sequence coding for the hproNGF-A A73Y/KG-RG peptide was PCR amplified by using a pair of specific primers (cloning primers) designed as follows:

```
                                        (SEQ ID NO. 9)
Forward Primer: 5' ATGGCCTCATCTAATGGACA 3'

(SEQ ID NO. 10)
Reverse Primer: 5' GGCTCTTCTCACAGCCTT 3'
```

The amplification product was then inserted in a specific linearised plasmid vector, pFastBac™/CT-TOPO®, containing Vaccinia virus DNA topoisomerase I covalently bound to the 3' end of each DNA strand (referred to as "TOPO® activated" vector) using the Bac-to-Bac® C.HIS TOPO® Cloning Kit marketed by Thermo Scientific (Catalog Number: A11098) following the instructions supplied with the product. Insertion of the coding fragment in the plasmid was obtained in a test tube by blunt-end recombination catalysed by the topoisomerase enzyme. The above-described reaction provided a plasmid encoding the peptide according to the invention, to which a "tail" (tag) of six residues of the histidine amino acid (6×His) was added, which is required during purification of the recombinant protein.

The reaction product was then used to transform, by the heat-shock method, chemically competent One Shot® Mach1™ T1R E. coli bacteria, used for the multiplication of the plasmid vector, following the instructions contained in the Bac-to-Bac® C-HIS TOPO® Cloning Kit (Catalog number: A11098, Thermo Scientific). The transformed bacteria were then seeded on Petri dishes containing solid agarose medium with addition of ampicillin, required for the selection of recombinant bacteria, which through the plasmid have also incorporated the gene for resistance to this antibiotic. After the time required for bacterial growth (overnight at 37° C.), ampicillin-resistant colonies were selected, picked, and used for plasmid DNA isolation by using the PureLink® HiPure Mini Plasmid Purification Kit (Catalog Number: K210002 Thermo Scientific), following the instructions in the kit. The correctness of the direction of insertion was assessed by sequencing the expression clones with the primers supplied in the cloning kit at the "Sequencing Core Facilities of Eurofins Genomics" (Ebersberg, Germany) (FIG. 5). The purified plasmid was used to transform, by heat shock, competent MAX Efficiency® DH10Bac™ bacterial cells provided with the Bac-to-Bac® TOPO® Expression System kit (Catalog Number: A11100, Thermo Fisher). These cells, through proteins encoded by a helper plasmid contained therein, recombine by incorporating the pFastBac™/CT-TOPO® plasmid into a larger plasmid, called bacmid, which will subsequently be incorporated by transfection into insect cells (SF-9), thus making them able to produce a recombinant baculovirus containing the hproNGF-A encoding sequence. After the recombination reaction, the bacterial cells were cultured in liquid LB-AGAR medium according to the instructions supplied with the kit, and then the bacmid produced by them was purified by using the PureLink™ HiPure PlasmidMaxiprep Kit (Catalog Number: K210007, Thermo Scientific) following the instructions therein. The presence and correct orientation of the DNA sequence coding for the peptide according to the invention was assessed by PCR with specific sequencing primers included in the Bac-to-Bac® TOPO® Expression System kit (Catalog Number: A11100 Thermo Fisher).

EXAMPLE 4: PRODUCTION OF THE HPRONGF-A A73Y/KG-RG PEPTIDE IN SF-9 CELLS

The bacmid obtained as described in Example 3 was used to transfect, through the Cellfectin® II reagent (Catalog Number: 10362100, Thermo Scientific), SF-9 insect cells cultured in serum-free medium Sf-900 II SFM (Catalog Number: 10902088, Thermo Scientific).

The methodology indicated in the protocol for the use of the Cellfectin® II reagent (Catalog Number: 10362100, Thermo Scientific) and in the Bac-to-Bac® TOPO® Expression System (Catalog Number: A11100, Thermo Fisher), was followed for this purpose.

About 72 hours after transfection, the cell culture medium containing the recombinant baculovirus generated by the cells was clarified by centrifugation and plaque assayed, as described in the instructions of the Bac-to-Bac® TOPO® Expression System kit (Catalog Number: A11100, Thermo Fisher), to verify the infective titre of the virus produced. After verifying that the virus had a minimum titre of $10^7$CFU, this first viral stock (P1) was used to infect a larger amount of SF-9 cells which, in a manner similar to that described above, produced a second viral stock (P2) and simultaneously expressed the recombinant hproNGF-A A73Y/KG-RG peptide, which was released into the culture medium and purified as described below.

EXAMPLE 5: PURIFICATION OF THE HPRONGF-A A73Y/KG-RG PEPTIDE

In order to purify the peptide according to the invention, the culture medium from SF9 cells was centrifuged at 10000 g for 45 minutes and filtered with 0.2-micron low-protein-retention filters (Millex GP, Millipore), to remove the virus particles and/or cell fragments, and was contacted with a Ni-Sepharose resin (GE Healthcare), which selectively binds the 6×His fragments at the C-terminus of the recombinant protein. The resin, equilibrated with 20 mM phosphate buffer+0.5M NaCl+30 mM Imidazole (binding buffer), and the culture medium were mixed in a ratio of 1:5 v/v and subjected to orbital shaking at 200 rpm overnight at +4° C., to allow the 6×HIS residues to bind to the activated groups on the resin. After the binding, the resin was packed into a chromatography column (XK 16/20, GE Healthcare) and washed with 5 column volumes of the binding buffer. The protein was then eluted by subjecting the column to a 30 mM-500 mM imidazole gradient in 20 column volumes. The eluted protein was dialysed against ultrapure water for 24 hours, then the dialysed material was frozen and freeze-dried.

After the freeze-drying, the protein was resuspended at a concentration of 1 mg/ml in an appropriate buffer (50 mM Tris-HCl pH 7.5+150 mM NaCl+0.5 mM EDTA+1 mM DTT) and subsequently the Tobacco Etch Virus (TEV) protease (Catalog Number T4455, Sigma Aldrich) was added in a ratio of 100U protease per milligram of protein.

The TEV protease-mediated reaction is used to remove the 6×HIS tail (tag) linked to the C-terminus of the protein through a short amino acid bridge containing the site recognized by the TEV protease. For the enzymatic cleavage reaction, the reaction mixture was incubated at 30° C. for two hours and then dialysed overnight against 20 mM phosphate buffer+0.5 M NaCl+30 mM Imidazole (binding buffer). The dialysate was then loaded onto a Ni-Sepharose resin (GE Healthcare), which selectively binds the 6×His fragments at the N-terminus of the recombinant TEV protein. The resin, equilibrated with 20 mM phosphate buffer+ 0.5M NaCl+30 mM Imidazole (binding buffer), and the dialysate were mixed in a ratio of 1:5 v/v and subjected to orbital shaking at 200 rpm for 4 hours at +4° C., to allow the TEV 6×His residues to bind to the activated groups on the resin. After the binding, the resin was packed into a chromatography column (PD10, GE Healthcare) and washed with 5 column volumes of the binding buffer. Human recombinant hproNGF-AA73Y/KG-RG peptide from which the C-terminal 6×His fragments had been deleted is present in this wash. The eluted protein was dialysed against ultrapure water for 24 hours, thereafter the dialysed material was frozen and freeze-dried.

The lyophilisate was resuspended overnight in 25 mM Sodium Acetate pH 5.0+0.2 M NaCl. The dialysate was then loaded onto a SP-Sepharose FF 16/10 column (GE Healthcare) to further purify the hproNGF-A A73Y/KG-RG peptide by cation exchange chromatography. After loading the column and washing with 10 column volumes of 25 mM sodium acetate buffer pH 5.0+0.2 M NaCl, the hproNGF-A A73Y/KG-RG peptide was eluted with a 0.2-1 M NaCl gradient in 20 column volumes. The chromatographic peak corresponding to the hproNGF-A A73Y/KG-RG peptide was collected, dialysed for 24 hours against 20 litres of ultrapure water and subsequently frozen and freeze-dried.

The purity and specificity of the purified protein was assayed by SDS-PAGE and Western blot.

In short, a total of 1 μg of purified protein was treated with 4× loading buffer (62.5 mM Tris HCl pH 6.8, 20% (v/v) glycerol, 8% (w/v) SDS, 0.025% (w/v) bromphenol blue and 100 mM dithiothreitol) and heated to 90° C. for 5 minutes. The samples were resolved by SDS-PAGE electrophoresis in an 8-12% gradient polyacrylamide gel at 25-30 mA in running buffer (25 mM Tris HCl, 190 mM glycine adjusted to pH 8.3 and 0.1% (v/v) SDS). After the electrophoresis, the gel was transferred onto a nitrocellulose membrane overnight at 30 V in transfer buffer (25 mM Tris-HCl, 190 mM glycine adjusted to pH 8.3 and 20% (v/v) methanol) to perform the Western blot. The membranes on which the proteins were transferred from the polyacrylamide gel were rinsed in PBS+1% Tween 20 (T-PBS), blocked in T-PBS containing 5% non-fat freeze-dried milk for 1 hour at room temperature and then incubated overnight with appropriate primary antibodies at 4° C. The membranes were then extensively washed in T-PBS at room temperature and incubated with horseradish peroxidase (HRP)-conjugated secondary antibody. After the incubation, the binding of the secondary antibody to the primary antibody was detected with the enhanced chemiluminescence system (cod WBKLS0500, Millipore)(FIG. 6).

As shown in FIG. 6A, the parallel production of the native hproNGF-A peptide by means of the experimental procedures as described above resulted in extremely low yields, approximately 10 times lower than those obtained with the mutated peptide of the invention. In fact, the starting material being the same (same amount of culture medium of SF-9 cells infected with recombinant baculovirus), the yield is strongly affected by the degradation to which the native hproNGF-A peptide is subjected before it is released. Therefore, although at the end of the purification process described above both the native and mutated peptides can be obtained and isolated with satisfactory purity (FIG. 6B), the amount of hproNGF-A A73Y/KG-RG is 10 times higher than that of native hproNGF-A. FIG. 6A shows Western blot densitometry analysis of purified hproNGF-A wt and hproNGF-A A73Y/KG-RG, which reveals that almost 90% of the hproNGF-A A73Y/KG-RG protein remains intact following Ni-Sepharose column chromatography, whereas only 9% of native hproNGF-A remains in its 34 kDa form, since several molecular weight fragments of about 17, 13 and 6 kDa are generated in the producer cell, which represent the prevalence of NGF-immunoreactive material that can be seen after Ni-Sepharose column chromatography.

EXAMPLE 6: COMPARATIVE ANALYSIS BETWEEN HPRONGF-A A73Y/KG-RG PEPTIDE AND MATURE NGF

In order to assess the resistance of the hproNGF-A A73Y/KG-RG and mature NGF peptides to the action of extracellular proteases, rat pheochromocytoma cells (PC12) were stimulated with either of the two peptides. Samples collected from conditioned cell culture media at successive times (time zero; 4, 8 and 24 hours post-stimulation) were subjected to Western blot assay in order to verify the permanence of the hproNGF-A A73Y/KG-RG and NGF peptides in the culture medium.

The assay revealed that NGF remains in the culture medium for no more than 8 hours after the stimulus, (FIG. 7, left panel), whereas the hproNGF-A A73Y/KG-RG peptide is still present in the culture medium 24 hours after the stimulus (FIG. 7, right panel). These results clearly demonstrate the significant lower susceptibility of the hproNGF-A A73Y/KG-RG peptide to the action of extracellular proteases compared to the mNGF peptide.

EXAMPLE 7: ASSESSMENT OF THE BIOLOGICAL ACTIVITY OF THE PRONGF-A A73Y/KG-RG PEPTIDE

In order to perform a comparative analysis between the biological activity of the proNGF-A A73Y/KG-RG peptide according to the invention and the activity of the NGF peptide, an in vitro test was performed by using PC12 cells, which differentiate into the neuronal phenotype upon contact with neurotrophic factors such as, for example, mature NGF peptide.

PC12 cells were cultured in RPMI 1640 culture medium supplemented with 10% horse serum and 5% calf serum in a humidified atmosphere with 5% $CO_2$ at 37° C. The cells were then seeded on 6-well plates containing poly-L-Lysine, to allow adherence of the cells to the bottom of the well. The cells were washed three times to remove any trace of serum, maintained in serum-free culture medium for one hour and then exposed to serum-free medium containing 100 ng/ml mNGF or 250 ng/ml hproNGF-A A73Y/KG-RG. Stimuli were administered daily to the cell cultures for 5 days. After the five-day treatment, both the cells exposed to NGF and those exposed to proNGF A-A73Y/KG-RG exhibited the characteristic extensions (neurites) that testify successful neuronal differentiation (as shown in FIG. 8A).

EXAMPLE 8: COMPARISON OF THE NEUROPROTECTIVE ACTIVITIES OF THE PRONGF-A A73Y/KG-RG PEPTIDE AND THE NATIVE PRONGF-A AND PRONGF-A KG-RG PEPTIDES

In order to compare the effectiveness of the different mutations introduced in proNGF-A peptide sequence in counteracting serum deprivation-induced cytotoxicity, PC12 cells were stimulated with conditioned media from cells transfected with plasmids containing sequences encoding either the native, non-mutated proNGF-A peptide (proNGF-A wt), or proNGF-A mutant containing the double mutation K175G/R176G (proNGF-A KG-RG), or the proNGF-A A73Y/KG-RG mutant of the invention. The cells were also stimulated with mature NGF (mNGF) and proNGF-A purified from mouse submandibular glands.

PC12 cells were cultured in RPMI 1640 culture medium supplemented with 10% horse serum and 5% calf serum in a humidified atmosphere with 5% CO$_2$ at 37° C. The cells were then seeded on 96-well plates containing poly-L-Lysine, to allow adherence of the cells to the bottom of the well. The cells were washed three times to remove any traces of serum, kept in serum-free culture medium for one hour and then exposed to serum-free medium containing 100 ng/mL mNGF or 250 ng/mL proNGF-A purified from mouse submandibular glands, or to conditioned medium of HeLa cells transfected with plasmids encoding recombinant human proNGF-A peptides (proNGF-A wt, proNGF-A KG-RG, proNGF-A A73Y/KG-RG). Each experimental condition was replicated in four different wells. The stimuli were administered daily to the cell cultures for 5 days under the above culture conditions. After the five-day serum-free treatment, the reagent CellTiter 96® Cell Proliferation Assay (MTT, Catalog Number: G4000, Promega) was added to the culture medium. After 4 hours from the addition of the reagent, cell viability was determined by recording the absorbance at O. D.=450 nm through a microplate spectrophotometer reader.

As shown in FIG. 8B, proNGF-A A73Y/KG-RG (bar 4) protected PC12 cells from serum deprivation-induced death (bar A vs bar B) comparably to stimulation with mature mNGF (bar 1). The protective effect found was also significantly superior to that exerted by proNGF-A purified from murine submandibular glands (bar 5). Lastly, the outcome of stimulation with proNGF-A A73Y/KG-RG appeared to be enhanced compared to cells stimulated with proNGF-A wt (bar 2) or proNGF-A KG-RG (bar 3).

The invention claimed is:

1. An isolated peptide consisting of the amino acid sequence SEQ ID NO:3.

2. The isolated peptide according to claim 1, which is encoded by nucleic acid sequence SEQ ID NO:4.

3. An isolated nucleic acid sequence comprising SEQ ID NO:4.

4. An expression vector comprising an isolated nucleic acid sequence according to claim 3.

5. A host cell comprising an expression vector according to claim 4.

6. A method for the preparation of a peptide, comprising the step of culturing a host cell according to claim 5 under suitable conditions and for a time sufficient for the expression of the peptide and, optionally, a step of recovering the peptide from the culture.

7. A method of promoting neuronal differentiation and/or neuronal survival in a subject, said method comprising administering to the subject an isolated peptide according to claim 1, wherein the subject is affected by a neurodegenerative disease and/or an epithelial/disease.

8. The method according to claim 7, wherein the neurodegenerative disease is an acute or chronic neurodegenerative disease selected from the group consisting of ischemic or hemorrhagic brain stroke, traumatic brain injury, intracranial hypertension, cerebral edema, perinatal, pediatric or adult hypoxia/ischemia, cerebral palsy, hypoxia/ischemia caused by cardiac arrest, drowning or hypothermia, Alzheimer's disease, Parkinson's disease, Huntington's Chorea, amyotrophic lateral sclerosis (ALS), progressive supranuclear palsy, frontotemporal dementia, dementia with Lewy body disease, Creutzfeldt-Jakob disease (CJD), Gerstmann-Straussler-Scheinker disease (GSS).

9. The method according to claim 7, wherein the disease is an epithelial disease selected from the group consisting of diabetic pressure ulcers, peripheral neuropathic ulcers, pressure sores in patients with myelomeningocele (spina bifida), skin ulcers due to infectious diseases (leprosy, AIDS), traumatic or neurothrophic corneal ulcers (neurotrophic keratitis) and inflammatory chronic skin ulcers and vasculitis ulcers.

10. A pharmaceutical composition comprising an isolated peptide according to claim 1, and at least one pharmaceutically acceptable vehicle, excipient and/or diluent.

11. The pharmaceutical composition according to claim 10, which is in a pharmaceutical form suitable for administration via the enteral, parenteral or topical route.

* * * * *

SEQUENCE LISTING

```
<160> NUMBER OF SEQ ID NOS: 11

<210> SEQ ID NO 1
<211> LENGTH: 296
<212> TYPE: PRT
<213> ORGANISM: Homo sapiens

<400> SEQUENCE: 1

Met Ala Ser Ser Asn Gly His Phe Asn Glu Val Leu Ala Ser Gly Arg
1               5                   10                  15

Ala Val Gln Gly Ala Gly Trp His Ala Gly Pro Lys Leu Ser Ser Ala
            20                  25                  30

Ser Gly Pro Asn Asn Ser Phe Thr Lys Gly Ala Ala Phe Tyr Pro Gly
        35                  40                  45

His Thr Glu Val His Ser Val Met Ser Met Leu Phe Tyr Thr Leu Ile
    50                  55                  60

Thr Ala Phe Leu Ile Gly Ile Gln Ala Glu Pro His Ser Glu Ser Asn
65                  70                  75                  80

Val Pro Ala Gly His Thr Ile Pro Gln Ala His Trp Thr Lys Leu Gln
                85                  90                  95

His Ser Leu Asp Thr Ala Leu Arg Arg Ala Arg Ser Ala Pro Ala Ala
            100                 105                 110

Ala Ile Ala Ala Arg Val Ala Gly Gln Thr Arg Asn Ile Thr Val Asp
        115                 120                 125

Pro Arg Leu Phe Lys Lys Arg Arg Leu Arg Ser Pro Arg Val Leu Phe
    130                 135                 140

Ser Thr Gln Pro Pro Arg Glu Ala Ala Asp Thr Gln Asp Leu Asp Phe
145                 150                 155                 160

Glu Val Gly Gly Ala Ala Pro Phe Asn Arg Thr His Arg Ser Lys Arg
                165                 170                 175

Ser Ser Ser His Pro Ile Phe His Arg Gly Glu Phe Ser Val Cys Asp
            180                 185                 190
```

```
Ser Val Ser Val Trp Val Gly Asp Lys Thr Thr Ala Thr Asp Ile Lys
    195                 200                 205
Gly Lys Glu Val Met Val Leu Gly Glu Val Asn Ile Asn Asn Ser Val
    210                 215                 220
Phe Lys Gln Tyr Phe Phe Glu Thr Lys Cys Arg Asp Pro Asn Pro Val
225                 230                 235                 240
Asp Ser Gly Cys Arg Gly Ile Asp Ser Lys His Trp Asn Ser Tyr Cys
                245                 250                 255
Thr Thr Thr His Thr Phe Val Lys Ala Leu Thr Met Asp Gly Lys Gln
            260                 265                 270
Ala Ala Trp Arg Phe Ile Arg Ile Asp Thr Ala Cys Val Cys Val Leu
        275                 280                 285
Ser Arg Lys Ala Val Arg Arg Ala
    290                 295
```

<210> SEQ ID NO 2
<211> LENGTH: 888
<212> TYPE: DNA
<213> ORGANISM: Homo sapiens

<400> SEQUENCE: 2

```
atggcctcat ctaatggaca ctttaatgaa gttttggcca gtggtcgtgc agtccaaggg      60
gctggatggc atgctggacc caagctcagc tcagcgtccg gacccaataa cagttttacc     120
aagggagcag cttttatcc tggccacact gaggtgcata gcgtaatgtc catgttgttc     180
tacactctga tcacagcttt tctgatcggc atacaggcgg aaccacactc agagagcaat     240
gtccctgcag acacaccat cccccaagcc cactggacta aacttcagca ttcccttgac     300
actgcccttc gcagagcccg cagcgccccg cagcggcga tagctgcacg cgtggcgggg     360
cagacccgca acattactgt ggaccccagg ctgtttaaaa agcggcgact ccgttcaccc     420
cgtgtgctgt ttagcaccca gcctcccgt gaagctgcag acactcagga tctggacttc     480
gaggtcggtg gtgctgcccc cttcaacagg actcacagga gcaagcggtc atcatcccat     540
cccatcttcc acaggggcga attctcggtg tgtgacagtg tcagcgtgtg ggtgggggat     600
aagaccaccg ccacagacat caagggcaag gaggtgatgg tgttgggaga ggtgaacatt     660
aacaacagtg tattcaaaca gtacttttt gagaccaagt gccgggaccc aaatcccgtt     720
gacagcgggt gccggggcat tgactcaaag cactggaact catattgtac cacgactcac     780
acctttgtca aggcgctgac catggatggc aagcaggctg cctggcggtt tatccggata     840
gatacggcct gtgtgtgtgt gctcagcagg aaggctgtga agagagcc                 888
```

<210> SEQ ID NO 3
<211> LENGTH: 296
<212> TYPE: PRT
<213> ORGANISM: Homo sapiens
<220> FEATURE:
<223> OTHER INFORMATION: proNGF-A A73Y/KG-RG

<400> SEQUENCE: 3

```
Met Ala Ser Ser Asn Gly His Phe Asn Glu Val Leu Ala Ser Gly Arg
1               5                   10                  15
Ala Val Gln Gly Ala Gly Trp His Ala Gly Pro Lys Leu Ser Ser Ala
            20                  25                  30
Ser Gly Pro Asn Asn Ser Phe Thr Lys Gly Ala Ala Phe Tyr Pro Gly
        35                  40                  45
His Thr Glu Val His Ser Val Met Ser Met Leu Phe Tyr Thr Leu Ile
```

```
              50                  55                  60
Thr Ala Phe Leu Ile Gly Ile Gln Tyr Glu Pro His Ser Glu Ser Asn
 65                  70                  75                  80

Val Pro Ala Gly His Thr Ile Pro Gln Ala His Trp Thr Lys Leu Gln
                     85                  90                  95

His Ser Leu Asp Thr Ala Leu Arg Arg Ala Arg Ser Ala Pro Ala Ala
                100                 105                 110

Ala Ile Ala Ala Arg Val Ala Gly Gln Thr Arg Asn Ile Thr Val Asp
                115                 120                 125

Pro Arg Leu Phe Lys Lys Arg Arg Leu Arg Ser Pro Arg Val Leu Phe
                130                 135                 140

Ser Thr Gln Pro Pro Arg Glu Ala Ala Asp Thr Gln Asp Leu Asp Phe
145                 150                 155                 160

Glu Val Gly Gly Ala Ala Pro Phe Asn Arg Thr His Arg Ser Gly Gly
                165                 170                 175

Ser Ser Ser His Pro Ile Phe His Arg Gly Glu Phe Ser Val Cys Asp
                180                 185                 190

Ser Val Ser Val Trp Val Gly Asp Lys Thr Thr Ala Thr Asp Ile Lys
                195                 200                 205

Gly Lys Glu Val Met Val Leu Gly Glu Val Asn Ile Asn Asn Ser Val
                210                 215                 220

Phe Lys Gln Tyr Phe Phe Glu Thr Lys Cys Arg Asp Pro Asn Pro Val
225                 230                 235                 240

Asp Ser Gly Cys Arg Gly Ile Asp Ser Lys His Trp Asn Ser Tyr Cys
                245                 250                 255

Thr Thr Thr His Thr Phe Val Lys Ala Leu Thr Met Asp Gly Lys Gln
                260                 265                 270

Ala Ala Trp Arg Phe Ile Arg Ile Asp Thr Ala Cys Val Cys Val Leu
                275                 280                 285

Ser Arg Lys Ala Val Arg Arg Ala
                290                 295

<210> SEQ ID NO 4
<211> LENGTH: 888
<212> TYPE: DNA
<213> ORGANISM: Homo sapiens
<220> FEATURE:
<223> OTHER INFORMATION: proNGF-A A73Y/KG-RG cDNA

<400> SEQUENCE: 4
atggcctcat ctaatggaca ctttaatgaa gttttggcca gtggtcgtgc agtccaaggg      60
gctggatggc atgctggacc caagctcagc tcagcgtccg gacccaataa cagttttacc     120
aagggagcag ctttctatcc tggccacact gaggtgcata gcgtaatgtc catgttgttc     180
tacactctga tcacagcttt tctgatcggc atacagtatg aaccacactc agagagcaat     240
gtccctgcag gacacaccat ccccaagcc cactggacta aacttcagca ttcccttgac      300
actgcccttc gcagagcccg cagcgccccg gcagcggcga tagctgcacg cgtggcgggg     360
cagacccgca acattactgt ggaccccagg ctgtttaaaa agcggcgact ccgttcaccc     420
cgtgtgctgt ttagcaccca gcctcccgt gaagctgcag acactcagga tctggacttc      480
gaggtcggtg gtgctgcccc cttcaacagg actcacagga gcggggggtc atcatcccat     540
cccatcttcc acaggggcga attctcggtg tgtgacagtg tcagcgtgtg ggttggggat     600
aagaccaccg ccacagacat caagggcaag gaggtgatgg tgttgggaga ggtgaacatt     660
```

```
aacaacagtg tattcaaaca gtactttttt gagaccaagt gccgggaccc aaatcccgtt      720
gacagcgggt gccggggcat tgactcaaag cactggaact catattgtac cacgactcac      780
acctttgtca aggcgctgac catggatggc aagcaggctg cctggcggtt tatccggata      840
gatacggcct gtgtgtgtgt gctcagcagg aaggctgtga aagagcc                    888
```

<210> SEQ ID NO 5
<211> LENGTH: 45
<212> TYPE: DNA
<213> ORGANISM: Artificial Sequence
<220> FEATURE:
<223> OTHER INFORMATION: Primer A73Y forward

<400> SEQUENCE: 5

```
gcttttctga tcggcataca gtatgaacca cactcagaga gcaat                       45
```

<210> SEQ ID NO 6
<211> LENGTH: 45
<212> TYPE: DNA
<213> ORGANISM: Artificial Sequence
<220> FEATURE:
<223> OTHER INFORMATION: Primer A73Y reverse

<400> SEQUENCE: 6

```
attgctctct gagtgtggtt catactgtat gccgatcaga aaagc                       45
```

<210> SEQ ID NO 7
<211> LENGTH: 36
<212> TYPE: DNA
<213> ORGANISM: Artificial Sequence
<220> FEATURE:
<223> OTHER INFORMATION: Primer K175G/R176G forward

<400> SEQUENCE: 7

```
caggactcac aggagcgggg ggtcatcatc ccatcc                                 36
```

<210> SEQ ID NO 8
<211> LENGTH: 36
<212> TYPE: DNA
<213> ORGANISM: Artificial Sequence
<220> FEATURE:
<223> OTHER INFORMATION: Primer K175G/R176G reverse

<400> SEQUENCE: 8

```
ggatgggatg atgacccccc gctcctgtga gtcctg                                 36
```

<210> SEQ ID NO 9
<211> LENGTH: 20
<212> TYPE: DNA
<213> ORGANISM: Artificial Sequence
<220> FEATURE:
<223> OTHER INFORMATION: Primer forward

<400> SEQUENCE: 9

```
atggcctcat ctaatggaca                                                   20
```

<210> SEQ ID NO 10
<211> LENGTH: 18
<212> TYPE: DNA
<213> ORGANISM: Artificial Sequence
<220> FEATURE:
<223> OTHER INFORMATION: Primer reverse

<400> SEQUENCE: 10

```
ggctcttctc acagcctt                                                     18
```

<210> SEQ ID NO 11
<211> LENGTH: 936
<212> TYPE: DNA
<213> ORGANISM: Artificial Sequence
<220> FEATURE:
<223> OTHER INFORMATION: Bacmide proNGF-A A73Y/KG-RG

<400> SEQUENCE: 11

```
atggcctcat ctaatggaca ctttaatgaa gttttggcca gtggtcgtgc agtccaaggg        60
gctggatggc atgctggacc caagctcagc tcagcgtccg gacccaataa cagtttacc        120 aagggagcag ctttctatcc tggccacact gaggtgcata gcgtaatgtc catgttgttc       180
tacactctga tcacagcttt tctgatcggc atacagtatg aaccacactc agagagcaat       240
gtccctgcag gacacaccat cccccaagcc cactggacta aacttcagca ttcccttgac       300 actgccttc gcagagcccg cagcgcccg gcagcggcga tagctgcacg cgtggcgggg        360 cagaccgca acattactgt ggaccccagg ctgtttaaaa agcggcgact ccgttcaccc        420
cgtgtgctgt ttagcaccca gcctccccgt gaagctgcag acactcagga tctggacttc       480
gaggtcggtg gtgctgcccc cttcaacagg actcacagga gcgggggtc atcatcccat       540 cccatcttcc acagggcga attctcggtg tgtgacagtg tcagcgtgtg ggttggggat       600
aagaccaccg ccacagacat caagggcaag gaggtgatgg tgttgggaga ggtgaacatt      660
aacaacagtg tattcaaaca gtactttttt gagaccaagt gccgggaccc aaatcccgtt      720
gacagcgggt gccggggcat tgactcaaag cactggaact catattgtac cacgactcac     780
acctttgtca aggcgctgac catggatggc aagcaggctg cctggcggtt tatccggata      840
gatacggcct gtgtgtgtgt gctcagcagg aaggctgtga aagagccaa gggcgaaaac      900 ttgtactttc aaggccatca ccatcaccat cactag                                936
```